(12) United States Patent
Lysgaard

(10) Patent No.: US 9,993,626 B2
(45) Date of Patent: Jun. 12, 2018

(54) MEDICAL BALLOON ASSEMBLY AND METHOD OF MAKING A MEDICAL BALLOON

(71) Applicant: Cook Medical Technologies LLC, Bloomington, IN (US)

(72) Inventor: Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 272 days.

(21) Appl. No.: 14/703,300

(22) Filed: May 4, 2015

(65) Prior Publication Data

US 2015/0328440 A1    Nov. 19, 2015

(30) Foreign Application Priority Data

May 13, 2014   (GB) .................................. 1408477.6

(51) Int. Cl.
| | | |
|---|---|---|
| *A61M 29/00* | (2006.01) | |
| *A61M 25/10* | (2013.01) | |
| *A61L 29/06* | (2006.01) | |
| *A61L 29/04* | (2006.01) | |

(52) U.S. Cl.
CPC ........ *A61M 25/10* (2013.01); *A61M 25/1029* (2013.01); *A61L 29/041* (2013.01); *A61L 29/06* (2013.01); *A61M 2025/1031* (2013.01); *A61M 2025/1075* (2013.01); *A61M 2025/1086* (2013.01); *A61M 2025/1088* (2013.01)

(58) Field of Classification Search
CPC .. A61M 29/00; A61M 25/10; A61M 25/1029; A61M 2025/1031; A61M 2025/1086; A61M 2025/1088
See application file for complete search history.

(56) References Cited

U.S. PATENT DOCUMENTS

| | | |
|---|---|---|
| 5,358,486 A | 10/1994 | Saab |
| 5,833,657 A | 11/1998 | Reinhardt et al. |
| 5,954,740 A | 9/1999 | Ravenscroft et al. |

(Continued)

FOREIGN PATENT DOCUMENTS

| | | |
|---|---|---|
| EP | 0768097 A2 | 4/1997 |
| GB | 2501065 B | 10/2013 |
| GB | 2501243 B | 10/2013 |

OTHER PUBLICATIONS

European Search Report for corresponding European Application No. 15275029.5, dated Oct. 9, 2015 (6 pages).

(Continued)

*Primary Examiner* — Victor Nguyen
(74) *Attorney, Agent, or Firm* — Brinks Gilson & Lione

(57) ABSTRACT

A medical balloon includes an outer layer and an inner layer. The outer layer has a surface texture or formation such as a scoring element. The inner layer is made of a reflow material which during production of the balloon from a raw tubing will soften and flow into internal recesses in the outer layer, thereby filling these recesses and providing support to the outer layer formations so as to avoid flattening of these formations during use of the balloon. The balloon can be manufactured in a single formation step from a raw tubing having the outer and inner reflow layer coextruded.

12 Claims, 4 Drawing Sheets

(56) References Cited

U.S. PATENT DOCUMENTS

| | | | | |
|---|---|---|---|---|
| 5,968,069 | A | * | 10/1999 | Dusbabek ............... A61F 2/958 604/96.01 |
| 7,147,817 | B1 | * | 12/2006 | Lim .................. A61M 25/1006 264/289.6 |
| 2002/0058960 | A1 | * | 5/2002 | Hudson .............. A61B 17/0057 606/192 |
| 2003/0004535 | A1 | | 1/2003 | Musbach et al. |
| 2003/0055449 | A1 | | 3/2003 | Lee et al. |
| 2006/0182873 | A1 | | 8/2006 | Klisch et al. |
| 2007/0016278 | A1 | | 1/2007 | Shippy, III et al. |
| 2007/0142772 | A1 | | 6/2007 | Deshmukh et al. |
| 2009/0005860 | A1 | | 1/2009 | Gale et al. |
| 2013/0261548 | A1 | * | 10/2013 | Aggerholm ........... A61M 25/10 604/103.08 |

OTHER PUBLICATIONS

Search Report for GB Application No. 1408477.6, dated Dec. 6, 2014 (4 pages).

\* cited by examiner

MEDICAL BALLOON ASSEMBLY AND METHOD OF MAKING A MEDICAL BALLOON

RELATED APPLICATIONS

The present patent document claims the benefit of priority to GB Patent Application No. 1408477.6, filed May 13, 2014, and entitled "MEDICAL BALLOON ASSEMBLY AND METHOD OF MAKING A MEDICAL BALLOON," the entire contents of each of which are incorporated herein by reference.

BACKGROUND

1. Technical Field Text

The present invention relates to a medical balloon, for example but not limited to a balloon used for angioplasty procedures, for valve repair procedures, for occluding vessels and for deploying an implantable medical device. The invention also relates to a method of making such a balloon.

2. Background Information

Medical balloons for performing medical procedures are well known in the art, for at least the procedures mentioned above. Often such balloons have a smooth outer surface, which is satisfactory for most applications. However, there are many instances where a balloon with a smooth outer surface can be disadvantageous, including for instance slippage of the balloon in a vessel or across a valve opening, slippage of a medical device carried on the balloon and so on. In order to mitigate such disadvantages, attempts have been made to form balloons with roughened or textured outer surfaces. This may be achieved, for instance, by blowing a raw tubing in a textured or shaped mold such that the raw tubing is inflated against the mold surface, acquiring the shape of the mold surface. A balloon which is textured or shaped in this manner, that is by shaping the wall thereof, will retain a thin balloon wall and thus maintain the same foldability and wrappability as a conventional balloon. However, although in theory such balloons can be inflated into the molded shape, in practice they tend to lose any surface roughness or texturing as a result of stretching of the balloon wall under inflation pressure. This smoothing and flattening effect becomes more pronounced the greater the pressure to which the balloon is inflated. Often, the balloon must be inflated to a high pressure, for instance to break through vessel plaque, to deploy an implantable medical device and so on, in which case the outer balloon surface can become virtually smooth.

One way to mitigate the loss of such texturing in a balloon is to form the texturing elements from solid material. However, doing so compromises the foldability and wrappability of the balloon, restricting the degree to which it can be compacted radially for delivery purposes. Furthermore, such structures compromise the flexibility of the balloon. Attaching elements to a balloon does not resolve all of these drawbacks as the attachment mechanisms present their own disadvantages, including the need for attachment components and so on.

Examples of prior art medical balloons can be found in US-2007/0076278, US-2003/0004535, U.S. Pat. No. 5,954,740, US-2006/0182873, U.S. Pat. No. 5,358,486 and US-2009/0005860.

BRIEF SUMMARY

The present invention seeks to provide an improved medical balloon and method of making such a balloon.

According to an aspect of the present invention, there is provided a medical balloon having a balloon wall encapsulating a balloon chamber, the balloon being expandable by inflating the chamber with inflation fluid; wherein the balloon wall is formed of at least two layers overlying one another, an outer layer formed of a material having a first softening or melting temperature and an underlying layer formed of a material having a second softening or melting temperature, wherein the second temperature is lower than the first temperature.

As will become apparent below, the provision of an underlying, or inner, layer to the balloon which has a softening or melting temperature lower than that of an overlying or outer layer of the balloon enables the underlying layer to fill any recesses or cavities in the outer layer, formed for instance for texturing, roughening or shaping of the balloon, in a manner such that the underlying layer will support the outer layer during subsequent inflation of the balloon and prevent stretching of the outer layer, as can occur in prior art devices.

Preferably, the underlying layer extends across the entire expanse of the overlying layer.

The overlying layer may be the outermost layer of the balloon, while the underlying layer may be the innermost layer of the balloon. It is not excluded, however, that the balloon could have additional layers thereto, even between the underlying and overlying layers.

The balloon could be one of: roughened, textured and shaped.

In an embodiment, the underlying layer is made of a reflow material, for example a polyolefin such as Admer™; while the overlying layer may be made of a polyamide such as Nylon, a polyether block amide such as Pebax™ or polyethylene terephthalate (PET).

According to another aspect of the present invention, there is provided a method of making a medical balloon, including the steps of: disposing a raw tubing of balloon material in a mold, the mold having an inner mold surface having a shape consistent with that of the balloon to be formed, the raw tubing having a wall formed of at least two layers overlying one another, an outer layer formed of a material having a first softening or melting temperature and an underlying layer formed of a material having a second softening or melting temperature, wherein the second temperature is lower than the first temperature; inflating the raw tubing simultaneously with subjecting the raw tubing to heat, said inflation causing the raw tubing to expand to the inner mold surface and to form the medical balloon; wherein the heat causes melting or softening of the underlying layer, whereupon the material of the underlying layer flows into any recesses or cavities in the overlying layer.

With this method, at the time of manufacture of the balloon, the underlying layer is made to soften or melt so as to flow relative to the overlying layer, so as to be able to flow into any recesses, cavities or interstices in the inner surface of the overlying layer.

Preferably, the underlying layer has a smooth inner surface, typically having the minimum surface area possible, which assists in supporting the overlying layer during use of the balloon.

Other features and advantages of the teachings herein will become apparent from the following description and drawings depicting the preferred embodiments.

BRIEF DESCRIPTION OF THE DRAWINGS

Embodiments of the present invention are described below, by way of example only, with reference to the accompanying drawings, in which.

DETAILED DESCRIPTION OF THE DRAWINGS AND THE PRESENTLY PREFERRED EMBODIMENTS

Figure 1:
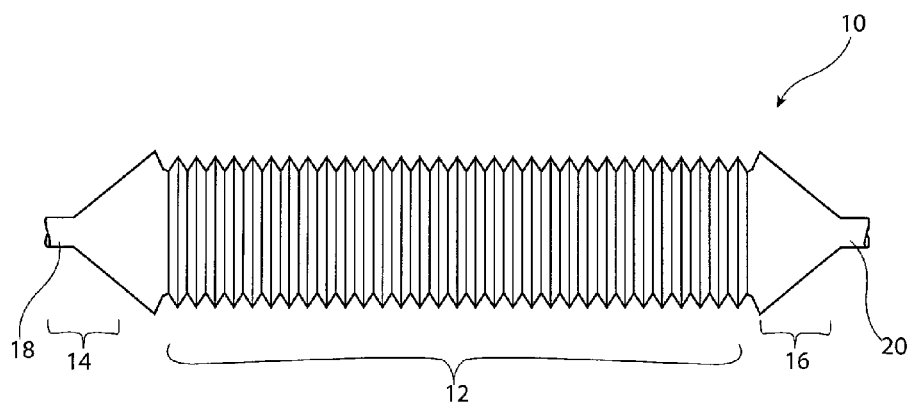
FIG. 1 is a schematic view of an example of roughened medical balloon.

Referring first to FIG. 1, this shows in schematic form a cross-sectional view of an example of medical balloon 10 having a body portion 12, of generally cylindrical form in this example, and first and second end cones 14 and 16 either side of the body portion 12. At the end of each cone portion 14, 16 there is a balloon neck 18, 20, the necks in practice fixed in fluid tight manner to a balloon catheter (not shown in the drawings). The balloon has an internal chamber which can be filled via a supply lumen in the balloon catheter with inflation fluid, typically saline solution or contrast media. When deflated, that is emptied of inflation fluid, the balloon 10 can be folded and wrapped around the balloon catheter, in a manner known in the art.

In the example shown in FIG. 1, the outer surface of the body portion 12 is roughened or textured in order to give the balloon 10 a non-smooth outer surface. Such texturing or roughening may be provided in order to seek to reduce the risk of slippage of the balloon 10 when deployed in a vessel or across a valve, and can equally be provided to seek to avoid slippage of a medical device carried on the balloon 10, such as a stent or stent graft. Such texturing can be contrasted with a balloon having a smooth outer surface, which can be slippery in use.

Figure 2A:
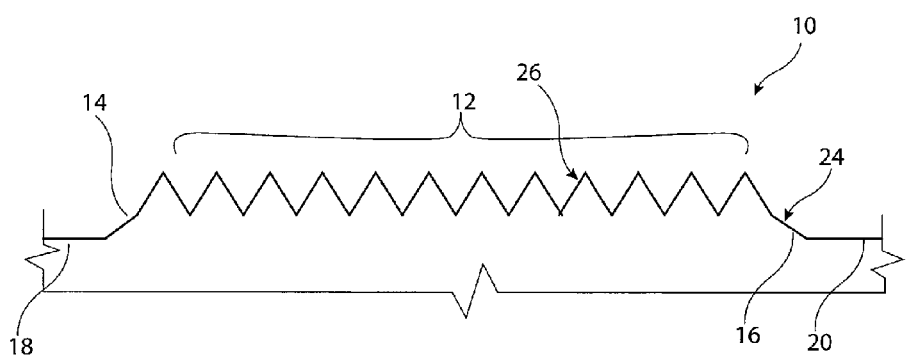
FIG. 2A is an enlarged view of a cross-section of a part of the balloon of FIG. 1.

Referring now to FIG. 2A, this shows in schematic form an example of texturing of the wall 24. As the skilled person will appreciate, FIG. 2A is a longitudinal cross-sectional view depicting a part of the balloon 10. The wall 24 is formed with a pattern of undulations or ribs 26 which create a roughened outer surface to the body portion 12 of the balloon. The undulations 26 are formed by shaping the balloon wall 24, for instance in a mold having an internal mold surface consistent with the undulations 26. Equally, the balloon wall 24 could be formed with an array of raised pimples and inwardly projecting dimples to create a more random roughening or texturing of the outer surface of the balloon wall 24, particularly in the body portion 12.

In this example, the roughening or texturing is formed solely in the balloon wall, which retains a thin and flexible balloon structure, enabling the balloon to be folded and wrapped tightly onto the balloon catheter. As explained above, alternative examples may add components to the outside of the balloon wall 24 to create such texturing or roughening, but at the expense of thickening the balloon wall, making the structure more complex and with loss of balloon flexibility and compressibility.

Figure 2B:
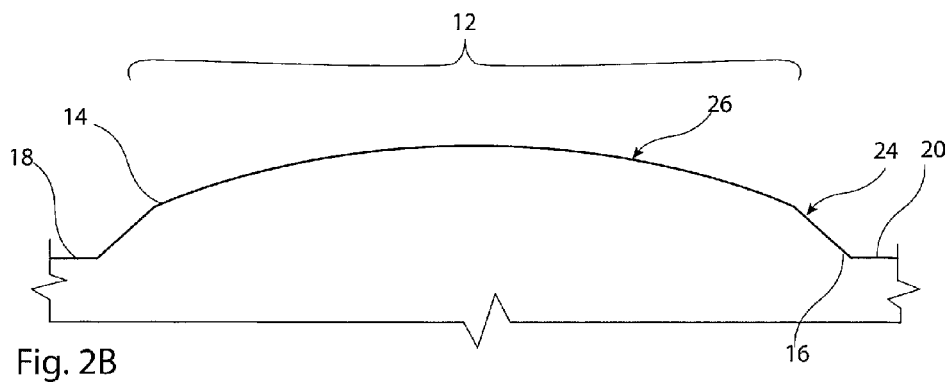
FIG. 2B is a schematic view of the cross-section of balloon depicted in FIG. 2A when the balloon is in an inflated condition.

Although in theory the shape of balloon depicted ion FIGS. 1 and 2A will have a roughened or textured outer surface, in practice this form is not retained when the balloon is inflated to a high pressure. Referring to FIG. 2B, this shows the section of balloon 10 depicted in FIG. 2A when the balloon has been inflated to a high pressure. As can be seen, the undulations 26 in the body portion 12 of the balloon 10 have been stretched out or smoothened as a result of the pressurisation of the balloon 10. The inventors have discovered that in practice a balloon of such a structure will become almost completely smooth on its outer surface when inflated to high pressures.

Figure 3A:
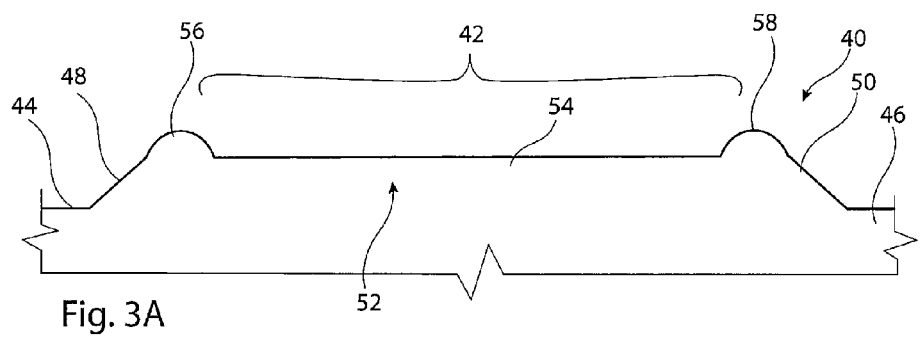
FIG. 3A is an enlarged view of a cross-section of a part of a shaped medical balloon.
Figure 3B:
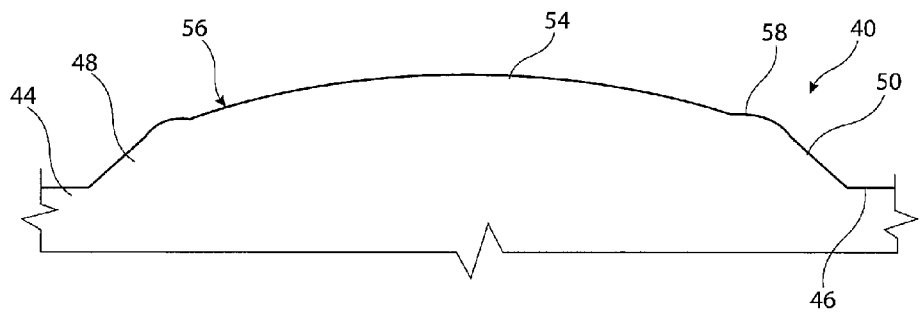
FIG. 3B is a schematic view of the cross-section of balloon depicted in FIG. 3A when the balloon is in an inflated condition.

FIG. 3A shows another example of balloon 40, in longitudinal cross-section. The balloon 40 has first and second necks 44, 46, which in practice are fixed in fluid tight manner to a balloon catheter, first and second end cones 48, 50 and between the end cones a body member 52. In this example, the body member 52 is designed to have a generally cylindrical section 54, for use for instance in supporting a medical device to be expanded and deployed via the balloon 40, and first and second circumferentially arranged ribs 56 and 58, used for holding the medical device on the balloon 40. As with the example of FIGS. 2A and 2B, the circumferential ribs 56, 58 are formed by suitably shaping the wall of the balloon 40. As with the example of FIG. 2A, though, as the balloon 40 is inflated to a high pressure, the body portion 42 will expand outwardly, causing the ribs 56, 58 to flatten. Thus, the retention function intended by the ribs 56, 58 is lost.

Figure 4:
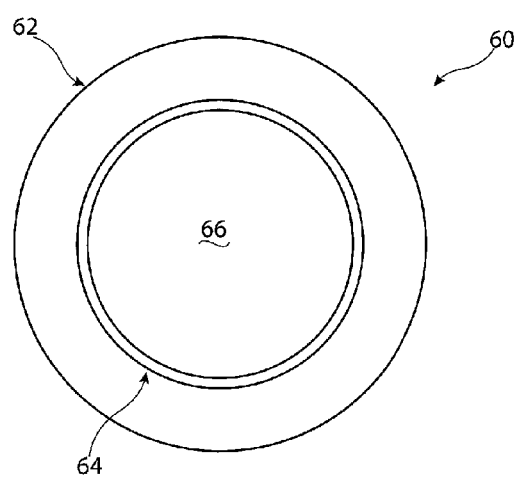
FIG. 4 is a schematic view in transverse cross-section of an embodiment of raw tubing according to the teachings herein.

Referring now to FIG. 4, this shows a transverse cross-sectional view of an embodiment of raw tubing 60 for forming a medical balloon according to the invention. The raw tubing 60 in this embodiment has an outer layer 62 of a conventional balloon material, for example a polyamide such as Nylon, polyether block amide such as Pebax™ or polyethylene terephthalate (PET). The raw tubing 60 also has an inner layer 64 made of a reflow material, that is a material having a lower melting or softening temperature than the material forming the outer layer 62. A suitable material for the inner layer is a polyolefin such as Admer™. Any polymer material having a softening or melting temperature less than that of the outer layer could be used. Ideally, the layer 64 of reflow material has a melting temperature around 10 degrees Centigrade lower than the melting temperature of the outer layer 62. The raw tubing 60 can usefully be a coextrusion of the layers 62, 64.

As is depicted in FIG. 4, the inner reflow layer 64 may in some embodiments be thinner than the outer layer 62. For instance, for the manufacture of a balloon having an inflated diameter of around 8 millimeters, a raw tubing having an outer diameter of 2.35 millimeters is suitable. That raw tubing may have an outer layer 62 which is 0.30 millimeters thick and an inner layer 64 which is 0.1 millimeters thick. In practice, the thickness of the reflow layer 64 will be dependent upon the nature of any texturing or shaping of the outer layer of the balloon, formed by the outer layer 62 of the raw tubing, and specifically enough to fill the internal voids created by such texturing with reflow material. In some embodiments, the amount of reflow material and hence the thickness of the layer 64 will be just sufficient to fill, or roughly enough substantially to fill, any internal voids created by texturing. In other embodiments the layer 62 is sufficient to retain a layer of reflow material around the entire inner area of the outer balloon layer 62, as will be explained in more detail below.

The structure of raw tubing 60 shown in FIG. 4 is the simplest embodiment for the balloon taught herein. It is not excluded, though, that there may be provided other layers to the balloon. For example, the outer layer of the balloon could be formed from a plurality of sub-layers. In another, embodiment there may be provided one or more layers inside the reflow layer 64, acting as the innermost layers to the balloon and in some embodiments at least having a melting temperature higher than the reflow material 64. It is preferred, however, that the balloon is formed from just two materials and a raw tubing 60 having just two layers.

In all embodiments of raw tubing, there is provided at least one internal lumen 66 for feeding blowing fluid into the raw tubing, as is described in further detail below.

Figure 5:
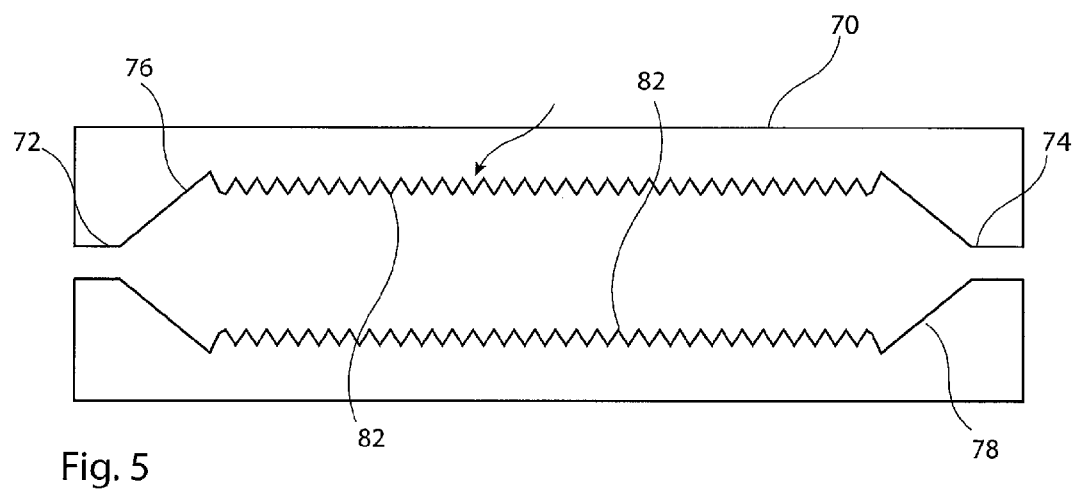
FIG. 5 is a schematic diagram of an embodiment of mold apparatus for forming a roughened or textured balloon according to the teachings herein.

Referring now to FIG. 5, there is shown in schematic form an example of mold apparatus for the manufacture of a medical balloon having a textured body portion. Only the principal components of the mold chamber 70 are depicted in the drawing, the other elements of the apparatus being conventional and therefore within the knowledge of the skilled person. The mold chamber 70 includes in this example first and second necks 72, 74 which hold the raw tubing in a radially constrained state, thereby to form the necks of the balloon. Next, the mold chamber 70 includes first and second conical sections 76, 78, which form the end cones of the balloon. The chamber 70 also includes a cylindrical section 80 which forms the body portion of the balloon and which in this example has a textured inner surface 82. The texturing could be of any desired form, including but not limited to roughening, ribbing and so on. This has the characteristic of an uneven surface 82, that is with raised and depressed areas in an arrangement consistent with the intended texturing of the outer surface of the formed balloon. In the example shown in FIG. 5, the conical sections 76, 78 have smooth inner surfaces but in other embodiments these could equally have textured inner surfaces.

The apparatus also includes, not shown in the drawing, fixing elements for fixing a length of raw tubing to the neck portions 72, 74, blowing and heating units for blowing inflation fluid into the lumen of the raw tubing and for heating the raw tubing and the mold chamber. The mold chamber is also typically of separable sections so that a formed balloon can be readily removed.

Figure 6:
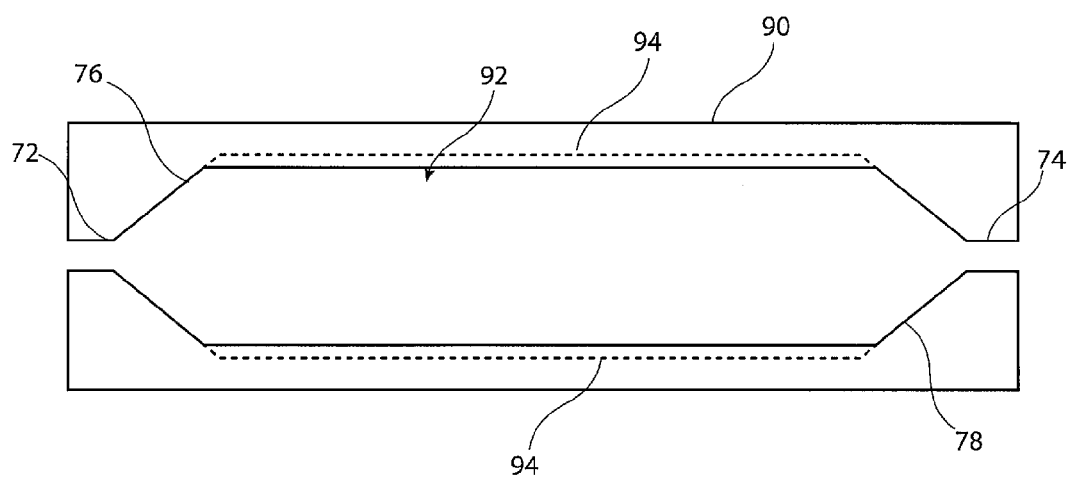
FIG. 6 is a schematic diagram of an embodiment of mold apparatus for forming a scoring balloon according to the teachings herein.

FIG. 6 shows another example of mold apparatus and in particular a mold chamber 90 similar to that of the example of FIG. 5 but in which the central cylindrical portion 92 is provided with a series of longitudinally extending grooves 94 in the inner surface of the chamber. The grooves 94 may be triangular in cross-section and extend parallel to the longitudinal axis of the of the cylindrical portion 92 of the mold chamber 90. There may be provided two, four or more such grooves.

The grooves 94 are designed to form triangular ribs along the outer surface of the body portion of a balloon which can act as scoring elements, in place of separate scoring or cutting elements which must later be attached or applied to a previously formed balloon.

The skilled person will appreciate that the grooves 94 could also extend along the conical portions 76, 78 of the mold chamber 90.

The other characteristics of the mold chamber of the example of FIG. 6 could be similar to those of the example of FIG. 5.

The method of manufacture of a medical balloon in either of the mold chambers 70, 90, and indeed any similar mold chamber, is generally the same and involves primarily a single manufacturing stage. A length of raw tubing 60 is fitted into the mold chamber 70, 90, such that the ends of the tubing 60 are retained in the necks 72, 74. One end of the raw tubing 60 is sealed and blowing fluid is then fed into the other end of the raw tubing 60 wither the tubing and/or mold being heated. The pressure of the blowing fluid and the softening of the material of the raw tubing 60 due by heating will cause the raw tubing 60 to expand within the mold chamber 70, 90 up to the inner walls of the conical sections 76, 78 and to the cylindrical section 80 or 92. The raw tubing 60, which may commence as an annular tubular structure, will expand in annular tubular manner, having the smallest transverse cross-sectional dimension, until the outer surface and in particular the outer layer 62 of the raw tubing 60 comes into contract with the inner surfaces of the sections 72, 74 and 80 or 92. In order to achieve this, the raw tubing 60 is preferably heated to the softening temperature of the outer layer 62 but less than its melting temperature.

When the raw tubing 60 comes into contact with the textured surface 82 or 92/94 of the cylindrical section 80 or 92 of the mold chamber, continued blowing pressure will press the outer layer 62 into the recesses in the mold surface 82,84, thereby causing the outer layer 62 to adopt the shape of the inner surface 82 or 94. At the same time, the inner layer 64 will expand under the blowing pressure but this will also be heated to a temperature at which it will flow, typically at around its melting temperature. The combined effect of the blowing pressure and the flowable condition of the inner layer 64 will cause the material inner layer 64 to flow into recesses formed in the inner surface of the outer layer 62 produced by the texturing of the inner mold surface, thereby to fill those recesses. The skilled person will appreciate that the inner surface of the raw tubing, even when expanded to the chamber walls, will tend to a smooth annular shape as a result of pressure equalisation within the chamber in the inflated raw tubing.

Once the raw tubing 60 has been fully expanded, thereby forming the balloon structure, it is allowed to cool and is then withdrawn from the mold after the blowing fluid has been released from within the chamber of the formed structure. The balloon form will retain the shape and texturing given that its layers will have cooled. The formed balloon can then be attached to a balloon catheter in known manner.

Figure 7:
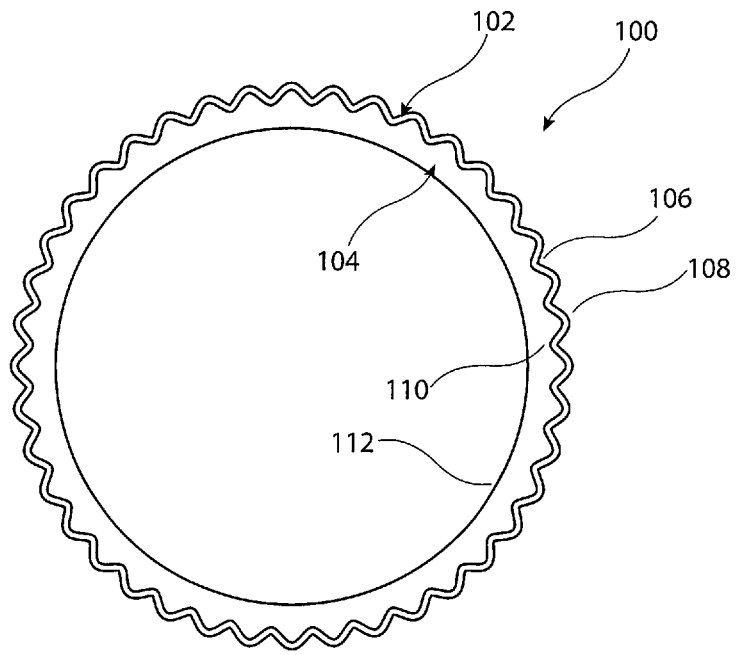
FIG. 7 is a cross-sectional view of a part of a scoring balloon made in the mold of FIG. 5.

Referring now to FIG. 7, this shows in transverse cross-section the structure of balloon wall of a balloon 100 produced in the chamber of FIG. 5. The balloon 100 has, in this example, an outermost layer 102 formed from the outer layer 62 of the raw tubing 60 and an inner layer 104 formed from the inner reflow layer 64 of the raw tubing 60. As can be seen in the Figure, the outer layer 102 is textured as per the inner surface 82, both at its outer surface 106 and at its inner surface 108. The outer layer 102 has a generally uniform wall thickness. The inner layer 104, on the other hand, has an outer surface 110 which, as a result of its reflow characteristic, has flowed into the recesses in the inner surface 108 of the outer layer 102 and which therefore is consistent with the texturing of the outer layer 102. On the other hand, the inner surface 112 of the inner layer 104 is generally round, having been expanded to this shape by the blowing fluid.

Figure 8:
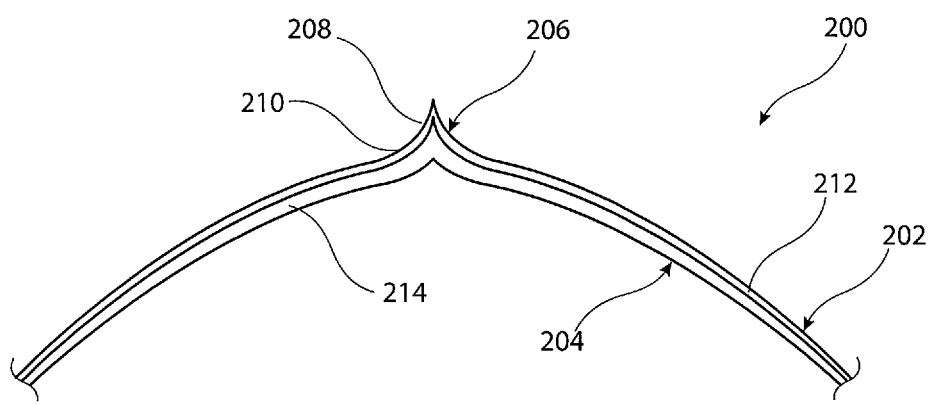
FIG. 8 is a schematic cross-sectional view of an embodiment of roughened balloon made by a mold similar to that shown in FIG. 6.

Referring to FIG. 8, this shows in transverse cross-section the structure of balloon wall of a balloon 200 formed using the chamber of FIG. 6. The balloon 200 has, in this example, an outermost layer 202 formed from the outer layer 62 of the raw tubing 60 and an inner layer 204 formed from the inner reflow layer 64 of the raw tubing 60. As can be seen in the Figure, the outer layer 202 has formed therein a rib or scoring element 206, at its outer surface 208, with a correspondingly shaped channel in its inner surface 210. The outer layer 202 has a generally uniform wall thickness. The inner layer 204, on the other hand, has an outer surface 212 which, as a result of its reflow characteristics, has flowed into the recesses in the inner surface 210 of the outer layer 202 of the formed scoring rib 206. On the other hand, the inner surface 214 of the inner layer 204 is generally round, having been expanded to this shape by the pressure of the blowing fluid. It will be appreciated that a balloon of FIG. 8 will typically have a plurality of scoring elements 206 disposed circumferentially around the balloon.

Thus, the reflow layer 64 of the raw tubing will flow during the balloon forming process into any recesses in the inner wall of the outer layer so as to fill those recesses. Once so filled and the balloon cooled to harden the reflow material, the reflow material will provide support to the recessed portions of the textured surface or scoring elements, for example, such that upon subsequent inflation of the balloon during its deployment, the outer layer 102, 202 will not stretch and flatten as occurs with prior art structures.

As discussed above, although in the examples shown in FIGS. 7 and 8 the inner layer of reflow material is continuous and extends across the entire inner periphery of the balloon chamber, this is not essential. In other embodiments, there may be provided less reflow material and in particular sufficient to fill or substantially fill, the recesses in the outer layer produced by texturing, shaping or other formations in the outer balloon layer. The reflow material will not only fill and bind to the outer layer so as to provide support thereto against flattening on inflation of the balloon, but will also help create a generally smooth inner surface to the balloon wall structure such that the inner surface of the balloon will have a minimal cross-sectional dimension in transverse cross-section, which will aid in pressure equalisation across the inner surface of the balloon.

The manufacturing process produces the balloon structure in a single step, which is therefore fast and efficient. Furthermore, the combination of outer and inner reflow layers need not impair significantly the foldability, wrappability or flexibility of the balloon. In particular, the reflow layer can be thin, not adding significant thickness to the balloon wall.

It is to be understood that the body portion of the balloon need not be cylindrical and could, for example, have other shapes such as being tapered from one end to the other, having a waist and so on.

Similarly, the texturing could be in the form of shaping to the balloon, for instance with circumferential ribs similar to those of the example of FIG. 3A.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A medical balloon comprising a balloon wall encapsulating a balloon chamber, the balloon being expandable by inflating the chamber with inflation fluid; wherein the balloon wall is formed of at least two layers overlying one another, an overlying layer formed of a material having a first softening or melting temperature and an underlying layer formed of a material having a second softening or melting temperature, wherein the second temperature is lower than the first temperature, wherein the overlying layer is roughened, textured or shaped, wherein the underlying layer has an inner surface which is generally round and an outer surface facing an inner surface of the overlying layer, the outer surface of the underlying layer having a shape which conforms to a shape of the inner surface of the overlying layer, and wherein the outer surface of the underlying layer extends into recesses or cavities in the inner surface of the overlying layer.

2. The medical balloon according to claim 1, wherein the overlying layer has an expanse and the underlying layer extends across the entire expanse of the overlying layer.

3. The medical balloon according to claim 1, wherein the overlying layer is an outer layer of the balloon.

4. The medical balloon according to claim 1, wherein the overlying layer is an outermost layer of the balloon.

5. The medical balloon according to claim 1, wherein the underlying layer is an inner layer of the balloon.

6. The medical balloon according to claim 1, wherein the underlying layer is an innermost layer of the balloon.

7. The medical balloon according to claim 1, wherein the underlying layer has an inner surface facing the chamber, the inner surface being smooth.

8. The medical balloon according to claim 1, wherein the underlying layer is made of a reflow material.

9. The medical balloon according to claim 1, wherein the underlying layer is made of polyolefin.

10. The medical balloon according to claim 1, wherein the overlying layer is made of polyamide.

11. A medical balloon comprising a balloon wall encapsulating a balloon chamber, the balloon being expandable by inflating the chamber with inflation fluid; wherein the balloon wall is formed of at least two layers overlying one another, an overlying layer formed of a material having a first softening or melting temperature and an underlying layer formed of a material having a second softening or melting temperature, wherein the second temperature is lower than the first temperature, wherein the overlying layer is roughened, textured or shaped, wherein the underlying layer has an outer surface facing an inner surface of the overlying layer, the outer surface of the underlying layer having a shape which conforms to a shape of the inner surface of the overlying layer, and wherein the outer surface of the underlying layer extends into recesses or cavities in the inner surface of the overlying layer; and wherein the overlaying layer has a uniform wall thickness.

12. The medical balloon according to claim 11, wherein the outer surface of the underlying layer has a surface roughness which is greater than a surface roughness of the inner surface of the underlying layer.

* * * * *